United States Patent [19]
Hines et al.

[11] Patent Number: 5,331,156
[45] Date of Patent: Jul. 19, 1994

[54] METHOD OF ANALYZING OIL AND WATER FRACTIONS IN A FLOW STREAM

[75] Inventors: Daniel R. Hines, Lawrence Ville, N.J.; Noboru Wada, Evergreen, Colo.; Stephen Garoff, Pittsburgh, Pa.; Oliver C. Mullins, Ridgefield, Conn.; Paul Hammond, Bourn; Jeffrey Tarvin, Great Shelford, both of England; Stephen P. Cramer, Palo Alto, Calif.; Ralphe Wiggins, Stamford, Conn.

[73] Assignee: Schlumberger Technology Corporation, New York, N.Y.

[21] Appl. No.: 15,708

[22] Filed: Feb. 9, 1993 (Under 37 CFR 1.47)

Related U.S. Application Data

[63] Continuation-in-part of Ser. No. 955,100, Oct. 1, 1992, Pat. No. 5,266,800.

[51] Int. Cl.$^5$ .................. G01F 5/00; G01F 1/74; G01N 21/35
[52] U.S. Cl. .................. 250/256; 250/301; 250/339.1; 250/343
[58] Field of Search ............... 250/301, 343, 256, 339

[56] References Cited

U.S. PATENT DOCUMENTS

| | | | |
|---|---|---|---|
| 4,707,603 | 11/1987 | Miemalä et al. | 250/339 |
| 4,994,671 | 2/1991 | Safinya et al. | 250/255 |
| 5,105,085 | 4/1992 | McGuire et al. | 250/343 |
| 5,107,118 | 4/1992 | Murray, Jr. et al. | 250/339 |

FOREIGN PATENT DOCUMENTS

| | | | |
|---|---|---|---|
| 53-148495 | 12/1978 | Japan | 250/343 |
| 256335 | 3/1970 | U.S.S.R. | 250/301 |

Primary Examiner—Constantine Hannaher
Attorney, Agent, or Firm—Leonard W. Pojunas; David P. Gordon

[57] ABSTRACT

Methods for quantifying the oil and water fractions of a fluid stream. A first method broadly includes making optical density (OD) measurements of the fluid stream by detecting photons of a first predetermined energy where the oil and water absorption characteristics are substantially identical (e.g., 1710 nm wavelength), and determining the oil and water fractions $f_o$ and $f_w$ according to $OD \simeq f_w \alpha_w l + f_o \alpha_o l$ where $\alpha_w$ and $\alpha_o$ are related to the absorption coefficients of the oil and water at the predetermined energy, l is the path width of the fluid stream, and $f_w + f_o = 1$. A second method which eliminates scattering effects utilizes the photons at the first predetermined energy and further utilizes photons of a second predetermined energy which is sufficiently close to the first predetermined energy such that the oil fraction is a linear function of the OD over the energy range. The oil and water fractions are then determined from the difference in optical density values ($\Delta OD$) according to $\Delta OD = f_o [(OD_{o,a} - OD_{o,b}) - (OD_{w,a} - OD_{w,b})] + (OD_{w,a} - OD_{w,b})$, where $OD_{o,a}$, $OD_{o,b}$, $OD_{w,a}$, and $OD_{w,b}$ are the optical densities per unit length of pure oil (o) and pure water (w) at the first (a) and second (b) wavelengths.

29 Claims, 11 Drawing Sheets

FIG. 1
FIG. 2
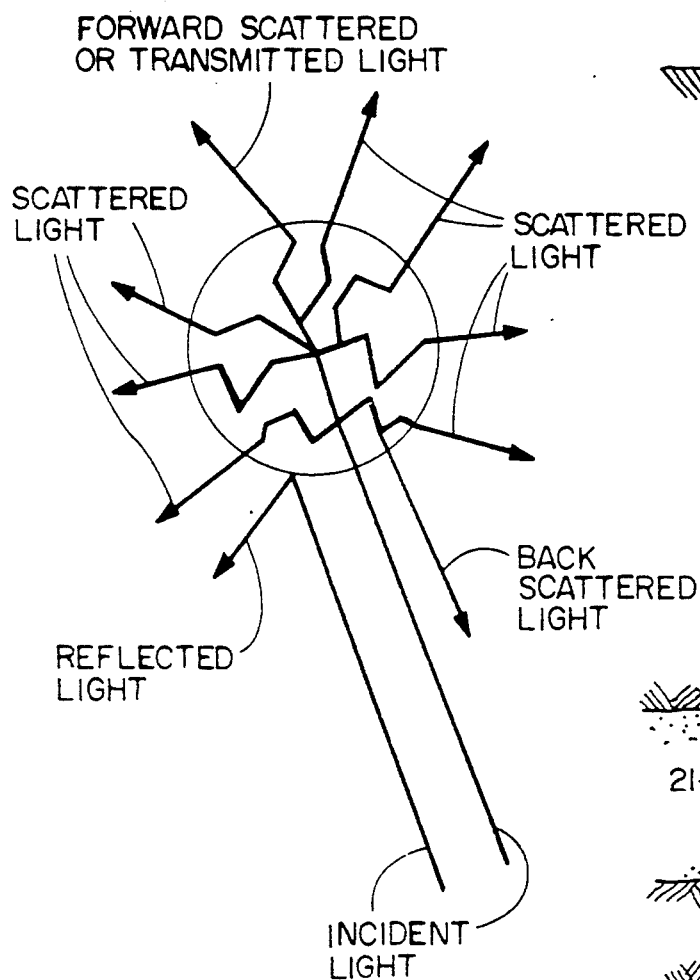
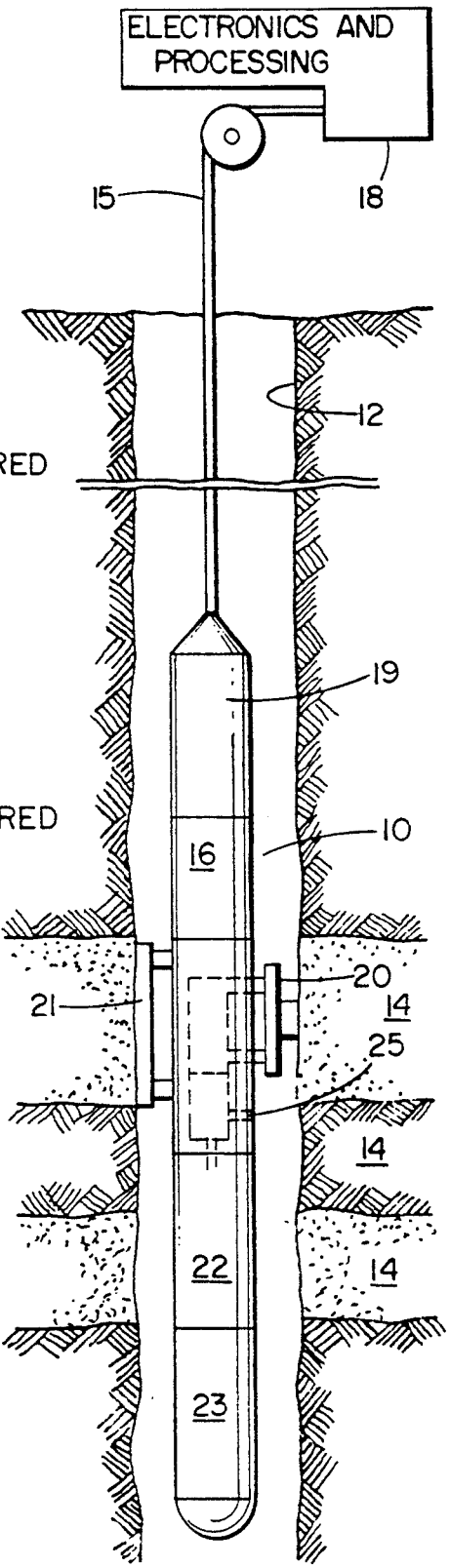

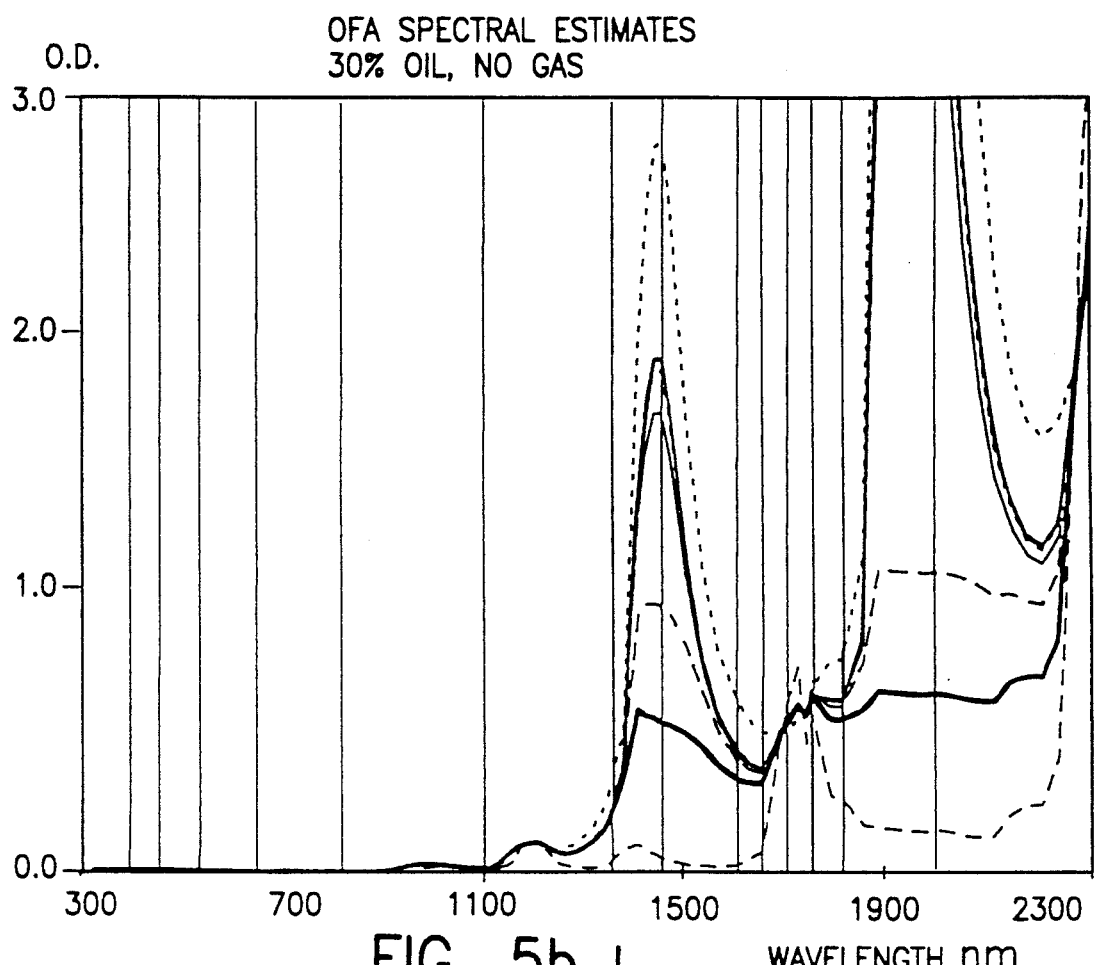
FIG. 5b-1
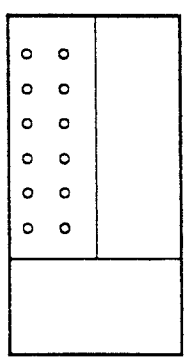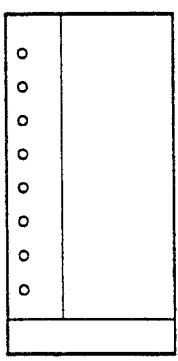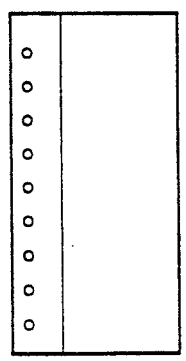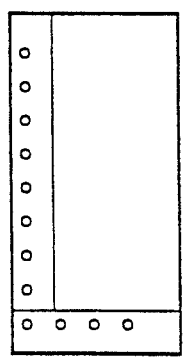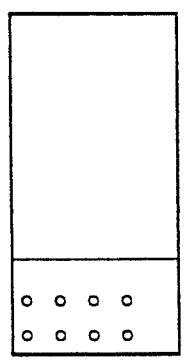
FIG. 5b-2

METHOD OF ANALYZING OIL AND WATER FRACTIONS IN A FLOW STREAM

This is a continuation-in-part of Ser. No. 07/955,100, filed Oct. 1, 1992, and assigned to the assignee hereof now U.S. Pat. No. 5,266,800.

BACKGROUND OF THE INVENTION

This invention relates to methods for analyzing oil and water fractions in a two phase flow stream. This invention further and more particularly relates to methods of determining the oil and water fractions of fluid flowing in a borehole.

As seen in FIG. 1, several different interactions may occur when light strikes a sample. Typically, if the sample is fluid, some light is reflected at the boundary of the sample while the rest of the light enters the sample. Inside the sample, light is scattered by phase interfaces, molecular excitations (Raman scattering) and by collective modes of the medium (e.g., Rayleigh scattering). In general, only a very small fraction of the light is scattered per centimeter of path by the Raman and Rayleigh scattering processes. Rather, depending upon the sample, much of the light is often absorbed. The absorption mechanisms of interest for the present invention are the vibrational absorptions which result from the excitation of overtones of molecular vibrations involving hydrogen atoms; not the electronic absorption which relates to the excitation of electronic transitions in aromatic molecules in the fluid such as asphaltenes, resins, and porphyrins.

Because different fluid samples absorb energy differently, the fraction of incident light absorbed per unit of pathlength in the sample depends on the composition of the sample and the wavelength of the light. Thus, the amount of absorption as a function of the wavelength of the light, hereinafter referred to as the "absorption spectrum", has been used in the past as an indicator of the composition of the sample. For example, in U.S. Pat. No. 4,994,671 to Safinya et al., assigned to the assignee hereof, and hereby incorporated by reference herein in its entirety, it is taught, among other things, that the absorption spectrum in the wavelength range of 0.3 to 2.5 microns can be used to analyze the composition of a fluid containing oil. The disclosed technique fits a plurality of data base spectra related to a plurality of oils and to water, etc., to the obtained absorption spectrum in order to determine the amounts of different oils and water that are present in the sample.

Numerous other techniques utilizing different parts of the spectrum are known in the arts for identifying or distinguishing between oils. For example, in U.S. Pat. No. 4,620,284 to Schnell, a helium-neon laser is used to provide photons of a 0.633 micron wave length which are directed at a sample. The resulting Raman spectrum which comprises scattered light at different wavelengths than the incident light is measured, and the measured spectrum is compared with previously obtained reference spectra of a plurality of substances in order to monitor fluid flowing through an oil refinery pipeline.

In U.S. Pat. No. 4,609,821 to Summers, especially prepared rock cuttings containing at least oil from an oil-based mud are excited with ultraviolet radiation with a 0.26 micron wave length, and the frequency and intensity of the resulting excited waves (fluorescence) which are at a longer wavelength than the incident radiation are detected and measured. By comparing the fluorescent spectral profile of the detected waves with similar profiles of the oil used in the oil-based mud, a determination is made as to whether the formation oil is also found in the rock cuttings.

In U.S. Pat. No. 3,896,312 to Brown et al., which is directed specifically to finding the source of a fuel oil leak or spill, crude oil samples are obtained and are prepared in a manner such that they are of the order of 0.1 mm thick. The crude oil samples are then analyzed to fine "fingerprint" valleys in the infrared spectra in the 600–1200 $cm^{-1}$ (8.3 to 16.6 micron wavelength), range, and are compared against a library of reference samples so as to identify which specific oil has been found among the different types of fuel oils.

While the Schnell, Summers, and Brown et al. techniques, and many other similar techniques of the prior art may be useful in certain very limited areas, it will be appreciated that they suffer from various drawbacks. For example, the use of laser equipment in Schnell severely restricts the environment in which the apparatus may be used, as lasers are not typically suited to harsh temperature and/or pressure situations such as a borehole environment. Also, the use of the Raman spectrum in Schnell imposes the requirement of equipment which can detect with very high resolution the low intensity scattered signals. The use by Summers of light having a 0.26 micron wavelength, and in Brown et al., of light in the 8.3 to 16.6 micron wavelength, severely limits the investigation of the samples to samples having nominal thickness. In fact, the Summers patent requires that the sample be diluted with solvents before investigation, while the Brown et al. patent requires that the sample be prepared to a thickness of 0.1 mm. Thus, the Summers and Brown et al. patents, do not permit an analysis of formation fluids, in situ. On the other hand, while the Safinya et al. disclosure is much less limited, and has been found to be generally useful in analyzing the composition of a formation fluid either in situ or at the surface, it will be appreciated that the interpretation techniques disclosed therein are computationally intensive. Particularly, large computing power is necessary to take a data base of spectra of numerous oils and water, and to fit those spectra to an obtained spectra in order to determine the compositional makeup of the sample. In downhole (in situ) situations, however, where the monitoring of a changing fluid flowstream in real time is desirable, and where it is less important to determine exactly the type of oil which is being obtained from the formation than it is to determine when the formation oil is being obtained as opposed to mud filtrate, it is advantageous to use less computationally intensive techniques.

It is of further note that the prior art techniques are not particularly suitable for analyzing two phase flow for the relative amounts of water and oil contained therein, and for distinguishing between two-phase slug and laminar flows.

SUMMARY OF THE INVENTION

It is therefore an object of the invention to provide computationally simple methods for determining the quantity of oil and water contained in a two phase fluid flow stream.

It is another object of the invention to provide methods for accurately determining the oil and water fractions of a fluid flow stream which may contain oil or water slugs or may be in laminar flow.

It is a further object of the invention to provide methods for determining the oil and water fractions of a fluid flow stream in a borehole flowing at rates of up to 10 cc/sec.

It is an additional object of the invention to utilize oil slug detection for providing a refined determination of the oil and water fractions in laminar flow sections of a fluid flow stream.

In accord with the objects of the invention, a simple method for quantifying the oil and water fractions of a fluid stream is provided and generally comprises making optical density measurements (OD) of the fluid stream by detecting photons of a first predetermined energy where the oil and water absorption characteristics are substantially identical, and based at least on the optical density measurements, determining the oil and water fractions. Preferably, in order to eliminate the effects of scattering on the oil and water fraction determinations, photons of a second predetermined energy which is close to the first predetermined energy and where the oil and water absorption characteristics are similar but not substantially identical (e.g., where the optical densities are within 0.5 optical density units of each other) are detected. The difference in absorption values is then used to determine the the oil and water fractions. Typically, the oil and water fractions are a linear function of the difference in absorption values.

While photons having wavelengths of 1200, 1710, or 1735 may define the photons of the first predetermined energy, the 1710 wavelength is preferred. When measuring photons at a wavelength of 1710 nm, a second photon wavelength located between 1650 and 1700 nm is preferred for defining the photons of the second predetermined energy.

According to another aspect of the invention, oil slugs are detected by detecting the optical density of photons at a wavelength of approximately 1900 nm. Based on the percentage of oil slugs in the flow stream, the total oil spectrum is adjusted, and the oil fraction in the laminar component of the flow stream is then determined according to the previously summarized techniques.

A better understanding of the invention, and additional advantages and objects of the invention will become apparent to those skilled in the art upon reference to the detailed description and the accompanying drawings.

BRIEF DESCRIPTION OF THE DRAWINGS

FIG. 1 is a diagram of some of the different interactions which may occur when light strikes a sample;

FIG. 2 is a schematic diagram of a borehole apparatus useful in conducting the methods of the invention;

FIG. 3b is a representation of the mixed oil and water flow stream of FIG. 3a;

FIGS. 5a–5e are graphs showing the optical absorption curves of flow streams containing different percentages of slug and laminar flows, where the oil content is constant at 10%, 30%, 50%, 70% and 90% respectively.

DETAILED DESCRIPTION OF THE PREFERRED EMBODIMENTS

Figures 1, 5A:
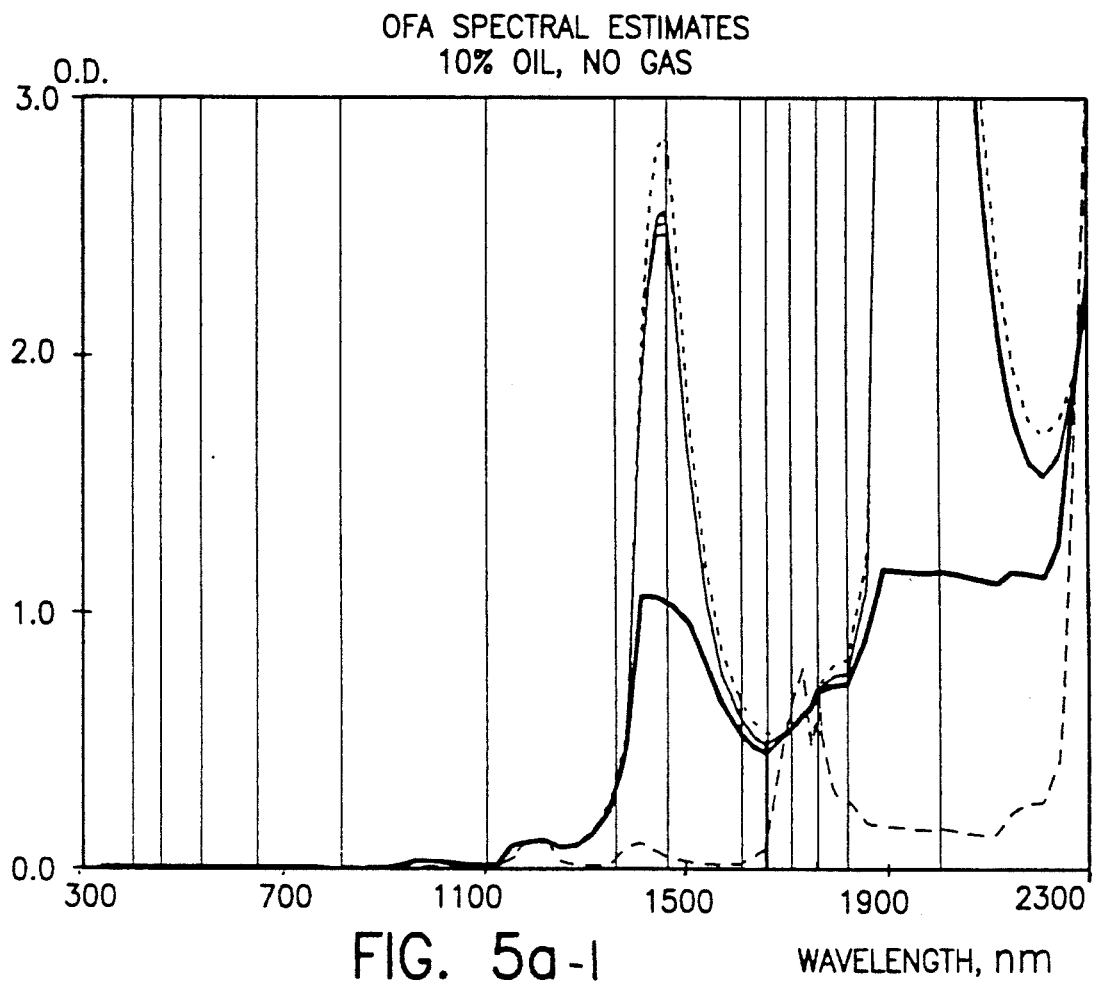
Figures 2, 5A:
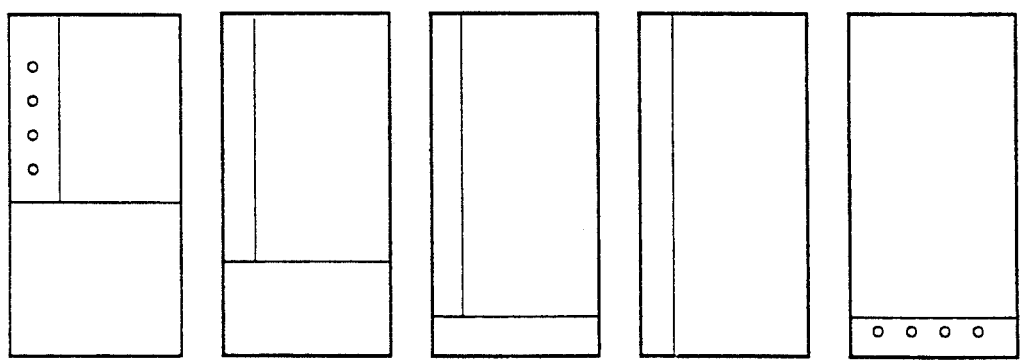

The instant invention is particularly applicable to both production logging and to borehole investigative logging. For purposes of brevity, however, the description herein will be primarily directed to borehole investigative logging, and the terms "borehole" and "borehole tool" should be read throughout the specification and claims to encompass a (cased) well and a tool used in a well, as well as in a borehole. Thus, a borehole tool 10 for testing earth formation and analyzing the composition of fluids from the formation 14 in accord with the invention is seen in FIG. 2. As illustrated, the tool 10 is suspended in the borehole 12 from the lower end of a typical multiconductor cable 15 that is spooled in the usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky and U.S. Pat. No. 4,396,259 to Miller which are hereby incorporated by reference herein. It should be appreciated, however, that it is not intended that the invention be limited to any particular method or apparatus for obtaining the formation fluids. Likewise, details of an apparatus particularly suitable for the method of the invention hereinafter described, are set forth in previously incorporated U.S. Pat. No. 4,994,671. Again, however, it is not intended that the invention be limited thereby. It is noted, however, that preferably, the borehole tool which is used to practice the preferred method of the invention includes a downhole processor (not shown) for carrying out arithmetic tasks as set forth below. Also, the borehole tool should preferably include an optical source for providing photons having energies defined by particular wavelengths as set forth below, and a means for determining the intensity of the light source at various wavelengths as well as the intensity of the light transmitted through the fluid sample at those wavelengths; i.e., spectral means for determining the absorption of the sample at a plurality of energy channels.

Figure 3A:
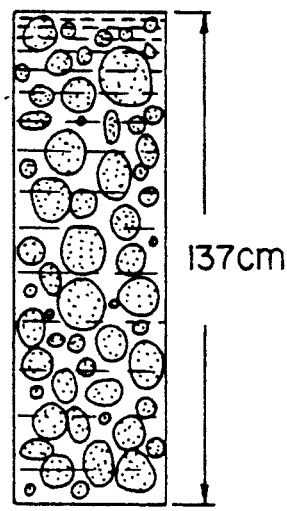
FIG. 3a is a representation of a fluid flow stream containing mixed oil and water.
Figure 3B:
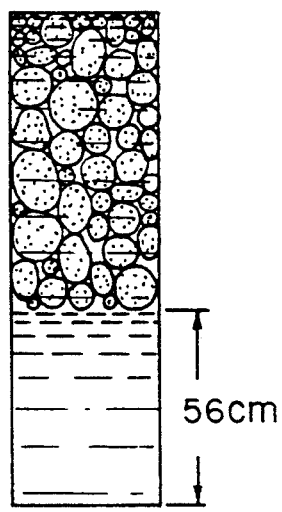
Figure 3C:
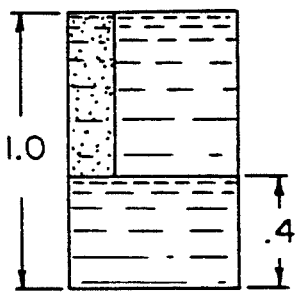
FIG. 3c is a refined representation of the fluid flow stream of FIG. 3a, where part of the flow stream is shown in laminar flow, and the remainder is shown with a water slug.

Turning to FIG. 3a, a typical flow stream likely to be encountered by the borehole tool is seen. In FIG. 3a, the fluid flow stream contains a mixture of oil and water, with the oil assuming the form of globules in the water. As light is directed through the fluid sample of FIG. 3a, it will be appreciated that some of the light will pass only through water, while other light will pass through both water and oil. Thus, the flow stream example of FIG. 3a can be rearranged as shown in FIG. 3b, to show a first percentage of the flow stream as being a water "slug", while the remainder of the flow stream includes the oil globules and water. A further refinement from FIG. 3b is seen in FIG. 3c, where the oil globules portion of the flow stream is divided out between oil and water in laminar flow, while the water slug remains. This representation is particularly helpful in understanding the manner in which light is absorbed by the flow stream. In particular, it will be appreciated that the transmission of light through water $(I/I_0)_w$ is defined by the absorption coefficient of water $\alpha'_w$ according to $$(I/I_0)_w = e^{-\alpha'_w l} \tag{1}$$

shere $I_0$ is the incident light, $I$ is the detected light, and $l$ is the width of the light path (flow stream). The absorption of water $A_w$ is then defined according to $$A_w = -\log(I/I_0)_w = a_w l \tag{2}$$

where $a_w = \alpha'_w \log_{10} e$. Similarly, the transmission of light through oil is defined by the absorption coefficient of oil $\alpha'_o$, such that $A_o = a_o l$.

In a laminar flow regime (i.e., water and oil side by side, the transmission (attenuation) of the light $I/I_0$ (i.e., detected light divided by incident light) is:

$$I/I_0 = e^{-f_w \alpha'_w l} e^{-f_o \alpha'_o l} \tag{3}$$

where $f_w$ is the water fraction and $f_o$ is the oil fraction. This may best be understood by the realization that if the flow stream is laminated, light first encounters one phase and then the other. For example, if light first encounters the water and then the oil, the amount of light reaching the oil is dictated by the transmission characteristics of the water (i.e., the first portion of equation (3) with $f_w$ times $l$ dictating the thickness or path length of the water lamination). The amount of the light attenuated by the water which then is detected after proceeding through the oil is dictated by the transmission characteristics of the oil (i.e., the second portion of equation (3) with $f_o$ times $l$ dictating the path length thickness of the oil lamination). Of course, the result is the same if the light first goes through the oil and then the water. In fact, the result is the same if the light goes through a series of oil, water, oil, water, etc. It should be noted that equation (3) does not account for scattering.

Where the flow stream domain is slug flow, the transmission of the light is defined according to:

$$I/I_0 = f_w e^{-\alpha'_w l} + f_o e^{-\alpha'_o l} \tag{4}$$

Here, since over a particular length of the flow stream subjected to the light, some light is going through water only (see e.g., the bottom portion of FIG. 3b), while other light is going through oil only, the transmission is additive. In other words, where there is an oil slug, the entire width of the flow stream is oil, and the amount of light being detected is dictated by the transmission characteristic of the oil only; and where there is a water "slug", the entire width of the flow stream is water, and the amount of light being detected is dictated by the transmission characteristic of the water. Because the light is shown through a window of defined length, at the edge of an oil slug, part of the light is going through only oil, while part of the light is going through only water. The amount of light detected will therefore be additive.

As stated above, it is an object of the invention to determine the quantities of oil and water flowing in a two phase liquid flow. However, without knowing the flow domain (i.e., laminar or slug) in advance, or without the understandings set forth hereinafter, one skilled in the art cannot use the above equations to make such a determination.

According to the invention, in order to solve for the quantities of oil and water flowing in a two phase liquid flow without knowing the flow domain, a mechanism for determining the fractions $f_w$ and $f_o$ independent of flow regime is required. It is realized by the inventors that where $\alpha'_w$ and $\alpha'_o$ are small, or their difference is small, equations (3) and (4) above reduce to the same equation where the only unknowns are the water and oil fractions which together add to one. Thus, as is explained hereinafter, by choosing a wavelength where the absorptions per unit length of water and oil are very similar (i.e., $\alpha'_w$ and $\alpha'_o$ are similar), a determination of the oil and water fractions can be made independent of flow regime.

The mathematics for showing that equations (3) and (4) substantially reduce to the same equation are as follows. Where $\alpha'_w$ and $\alpha'_o$ are small, a first order Taylor expansion of equation (3) for laminar flow results in:

$$I/I_0 = (1 - f_w \alpha'_w l)(1 - f_o \alpha'_o l) \tag{5}$$

Multiplying out the right hand of equation (5) yields:

$$\simeq 1 - f_w \alpha'_w l - f_o \alpha'_o l \tag{6}$$

as the last term is dropped as being negligible. Likewise, a first order Taylor expansion of equation (4) for slug flow results in:

$$I/I_0 = f_w(1 - \alpha'_w l) + f_o(1 - \alpha'_o l) \tag{7}$$

Multiplying out the right hand of equation (7) yields:

$$\simeq f_w - f_w \alpha'_w l + f_o - f_o \alpha'_o l \tag{8}$$

$$\simeq 1 - f_w \alpha'_w l - f_o \alpha'_o l \tag{9}$$

It will be appreciated that equations (6) and (9) are equivalent. It will also be appreciated by those skilled in the art that similar mathematics applies where instead of $\alpha'_w$ and $\alpha'_o$ being small, their difference is small. Thus, according to the invention, as long as the absorptions of the oil and water are similar, all that is required to determine the water and oil fractions is to find the absorption and solve equation (6) or (9), recognizing that $f_w = 1 - f_o$. Thus, it is necessary to find and utilize wavelengths where the absorptions of oil and water are similar.

Figure 4A:
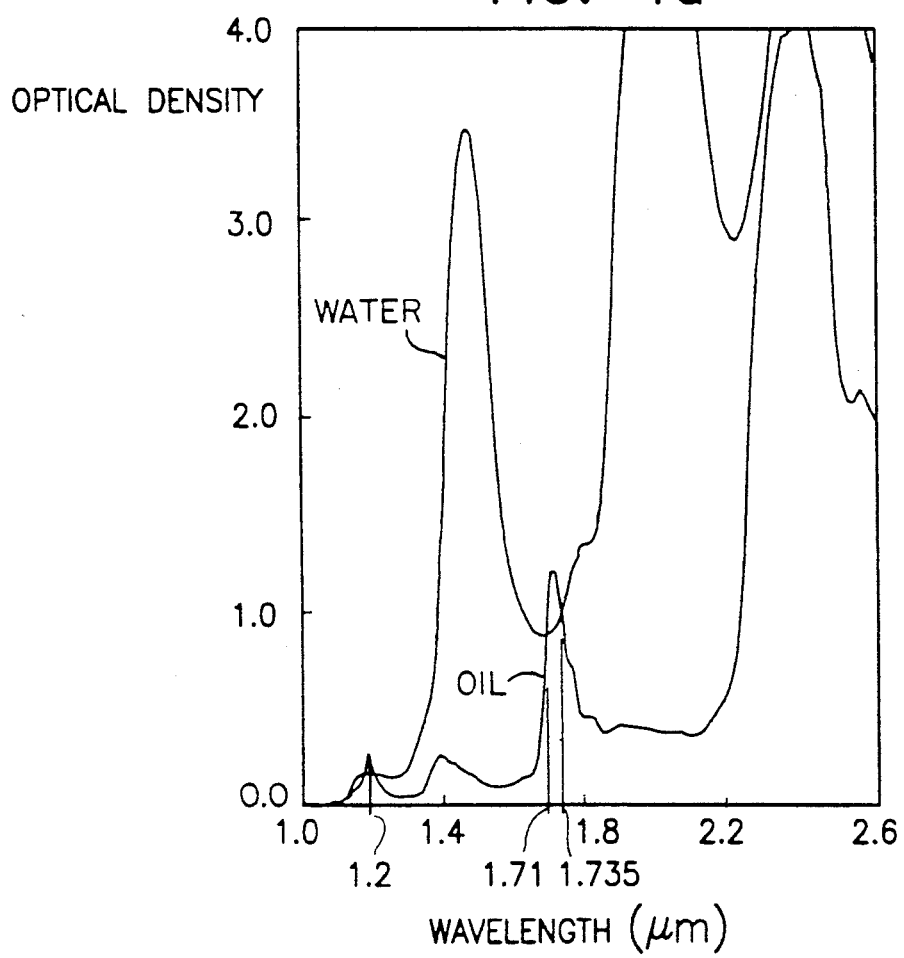
FIG. 4a is a graph showing the optical absorption curves of oil and water as a function of wavelength.

Turning to FIG. 4a, the optical density (absorption) curves of oil and water are seen plotted as a linear scale as a function of wavelength. As seen in FIG. 4a, the oil and water have almost identical absorptions at wavelengths of 1200, 1710, and 1735 and 1735 nanometers.

In fact, the absorptions of oil and water are sufficiently similar in small ranges around the 1200, 1710, and 1735 nanometer wavelengths that wavelengths in those small ranges could be utilized. Indeed, it is possible to use other wavelengths in the range around the 1200, 1710, and 1735 nanometers as will be discussed hereinafter with reference to FIGS. 5a-5e, provided the flow regime does not substantially affect the absorption characteristics determined.

Figure 4B:
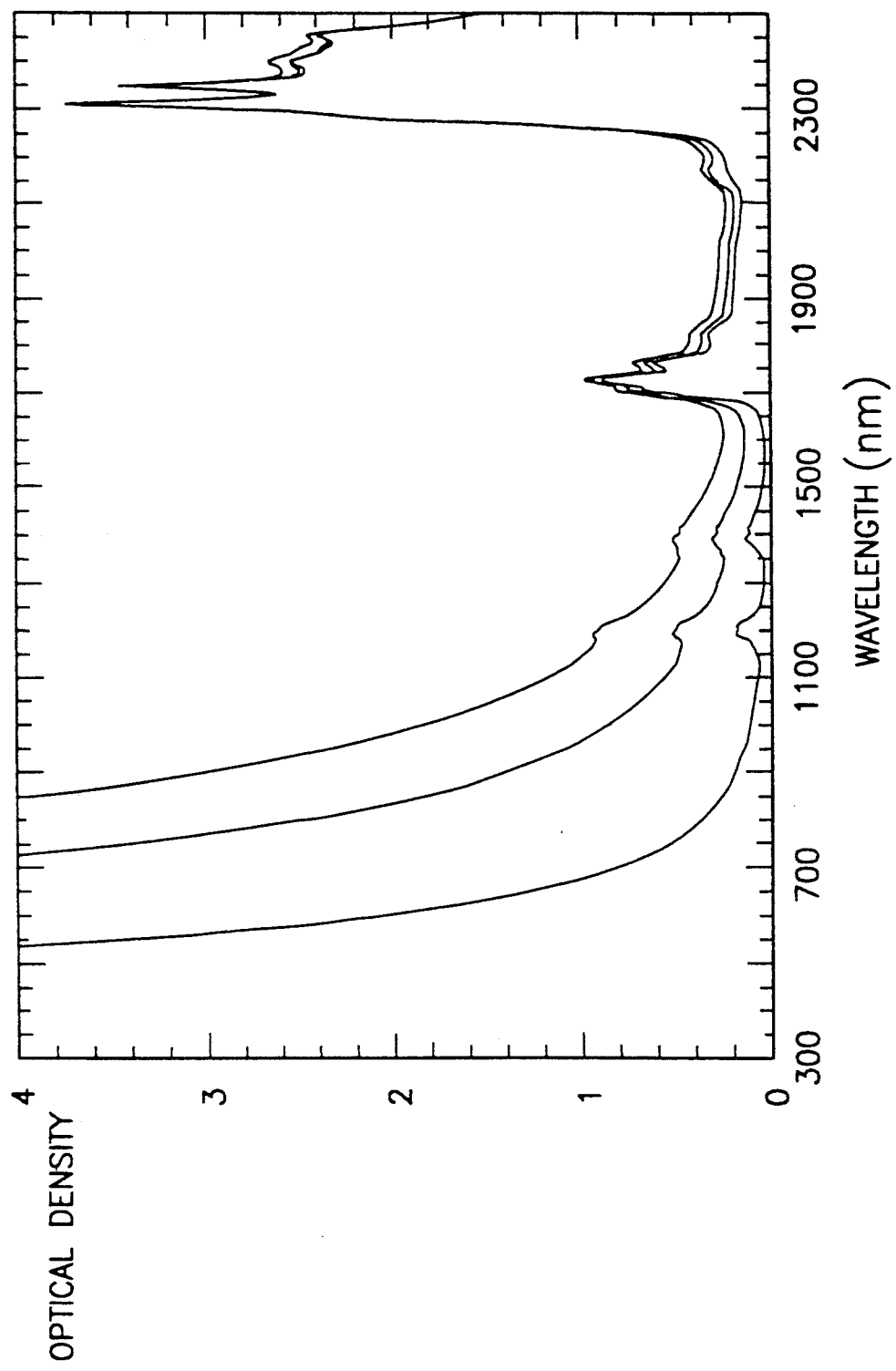
FIG. 4b is a graph showing the absorption spectra of three different oils.

Of the three wavelengths where the oil and water have almost identical absorptions, the 1710 nanometer wavelength is preferred for various reasons. First, it is desirable to choose a wavelength where the color of the oil will not affect the absorption. As seen in FIG. 4b, below 1500 nanometers, the color of oil can be a factor as the absorption spectra of the oils is different and only superimpose at the vibrational overtone peaks above 1500 nanometers. Thus, the 1200 nanometer wavelength is not optimal for that reason. Also, because salinity and temperature can affect the absorption, it is desirable that the wavelength utilized not be located at a point where the water spectrum is fluctuating greatly. Thus, the 1710 nanometer wavelength is preferred over the 1735 nanometer wavelength, because, as can be seen in FIG. 4a, the 1710 wavelength is located in a valley of the optical density spectrum of water, while the 1735 nanometer wavelength is located on a rising edge of the spectrum. A small movement of the water spectrum due to salinity or temperature could cause a large change of the optical density at the 1735 nanometer wavelength, while such a movement at the 1710 nanometer wavelength is not likely to have more than a small effect.

As aforementioned, photon absorption is not the only mechanism which affects optical density; scattering of photons also affects the amount of light which is detected (i.e., optical density equals absorption plus scattering). In order to remove the affect of scattering, it is desirable to detect the optical density of the fluid sample at two different wavelengths, with one of the wavelengths preferably being 1710 nanometers (or 1200 or 1735 nanometers) as discussed above. According to one embodiment of the invention, the other wavelength is chosen to be a wavelength where no absorption is expected (e.g., 1100 nanometers). If there is no absorption, then any optical density reading obtained at that wavelength can be assumed to be as a result of scattering. The scattering effect, which is assumed to be constant over all wavelength channels of interest, may then be removed from the optical density measurement by subtracting the scattering if the optical density is described in log form (i.e., $OD = \log I/I_0 = A+S$), or by dividing where expressed in linear form (i.e., $I/I_0 = e^{-a1S}$) prior to solving for water and oil fractions. It is of note, that generally, the scattering effect is constant over all wavelength channels of interest. However, where fines are flowing in the flow stream, which is not uncommon during borehole "drawdown" techniques or during initial production, the fines may affect the scattering as a function of wavelength. It is therefore desirable to wait until after the fines stop flowing in order to make the measurements.

According to another embodiment of the invention, scattering of photons can be accounted for by finding the optical density of the fluid in two energy channels, and subtracting the results in order to reduce or eliminate scattering effects. In order for this technique to work properly, the wavelengths at which the optical density measurements are made should be chosen such that the absorption is substantially linear with the oil (or water) fraction of the flow stream. If that is the case, the difference between the measured optical densities ($\Delta OD$) can be defined by:

$$\Delta OD = f_o(OD_{o,a} - OD_{o,b}) + f_w(OD_{w,a} - OD_{w,b}) \quad (10)$$

where $OD_{o,a}$, $OD_{o,b}$, $OD_{w,a}$, and $OD_{w,b}$ are respectively the optical densities per unit length of pure oil at a first wavelength and at a second wavelength, and the optical densities per unit length of pure water at the first and second wavelengths. Recognizing that $f_o + f_w = 1$, equation (10) can be arranged as:

$$\Delta OD = f_o[(OD_{o,a} - OD_{o,b}) - (OD_{w,a} - OD_{w,b})] + (OD_{w,a} - OD_{w,b}) \quad (11)$$

Since the optical densities of pure oil and pure water at the wavelengths of choice are known, and the delta optical density is measured, the oil fraction, and hence the water fraction are simply determined according to equation (11). Of course, as previously mentioned, this is true provided the absorption is linear with the oil and water fractions over the wavelengths of choice. It should be noted relative to equation (ii), that where the oil fraction is zero, the equation reduces to the difference in optical density being the difference in the optical density of water at the chosen wavelengths; and where the water fraction is zero ($f_o = 1$), the equation reduces to the difference in optical density of oil at the chosen wavelengths.

Figures 1, 5C:
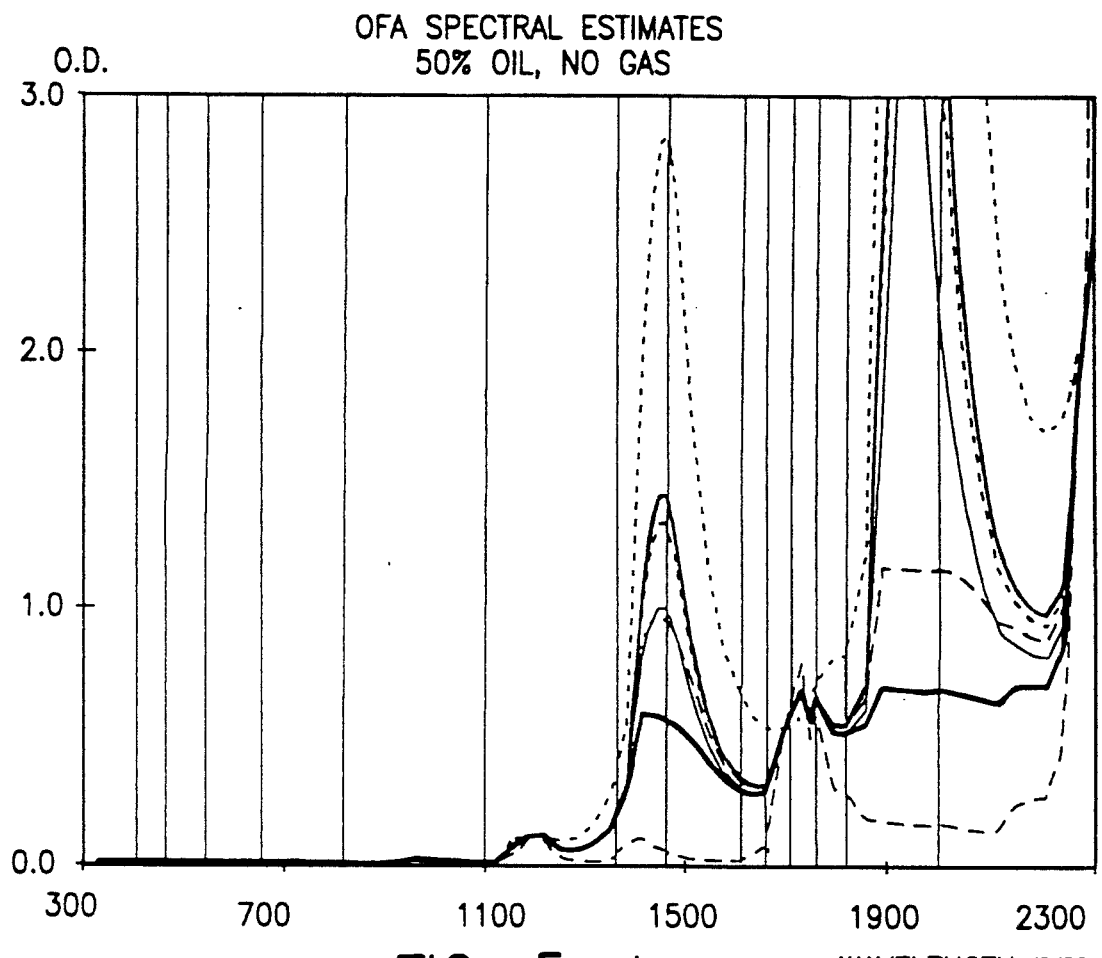
Figures 2, 5C:
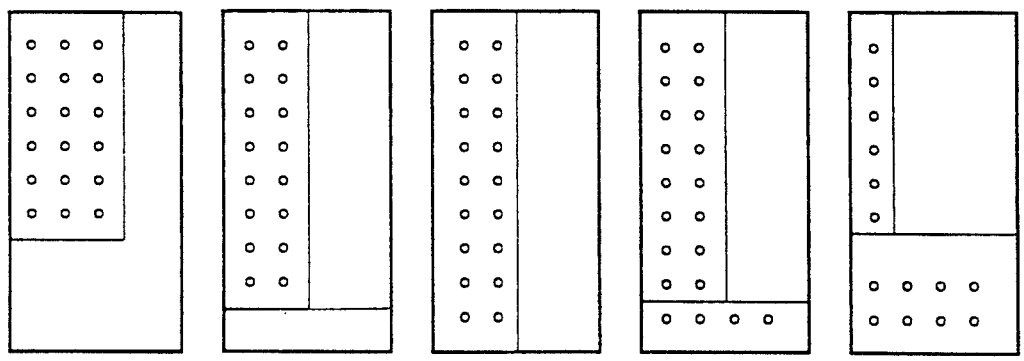
Figures 1, 5D:
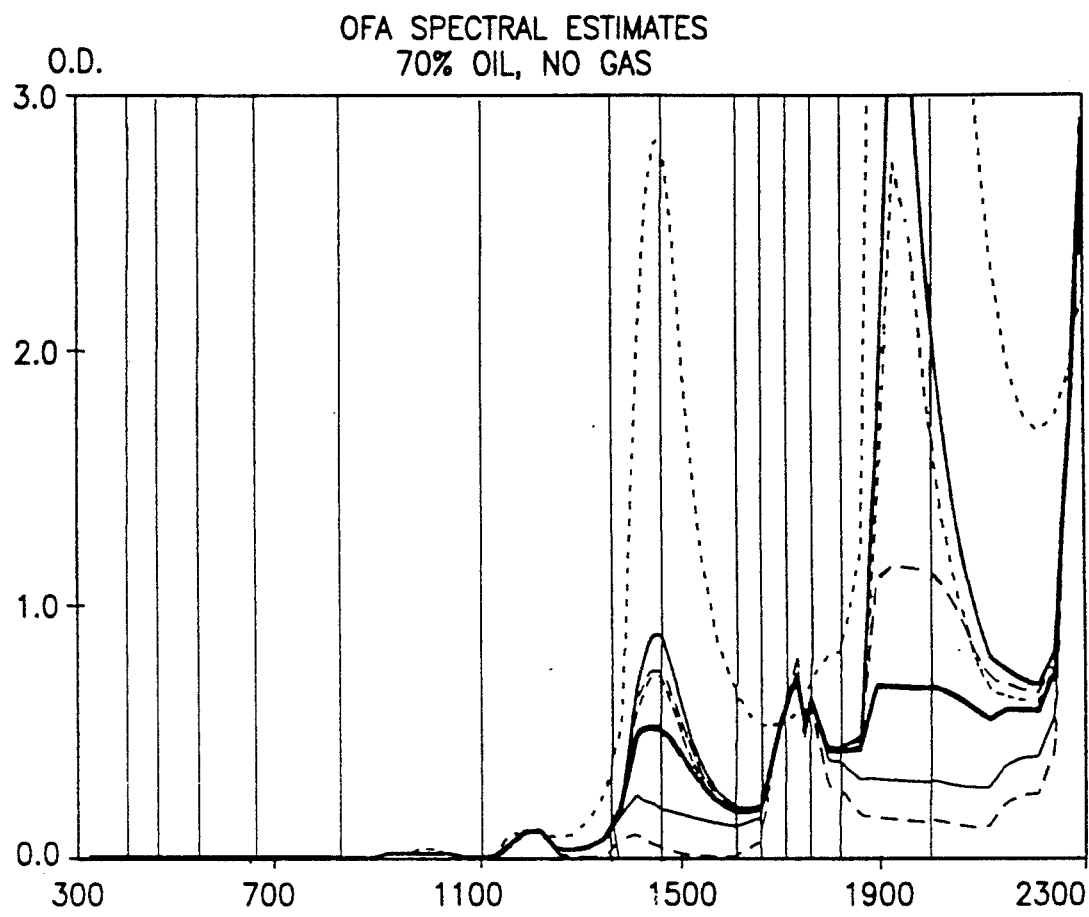
Figures 2, 5D:
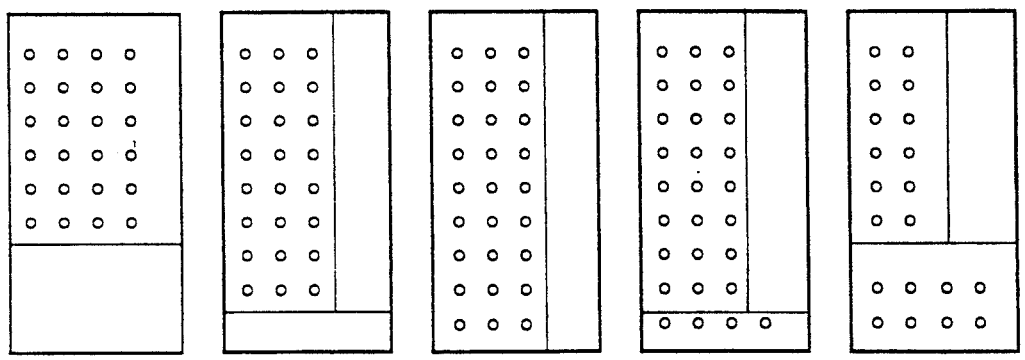
Figures 1, 5E:
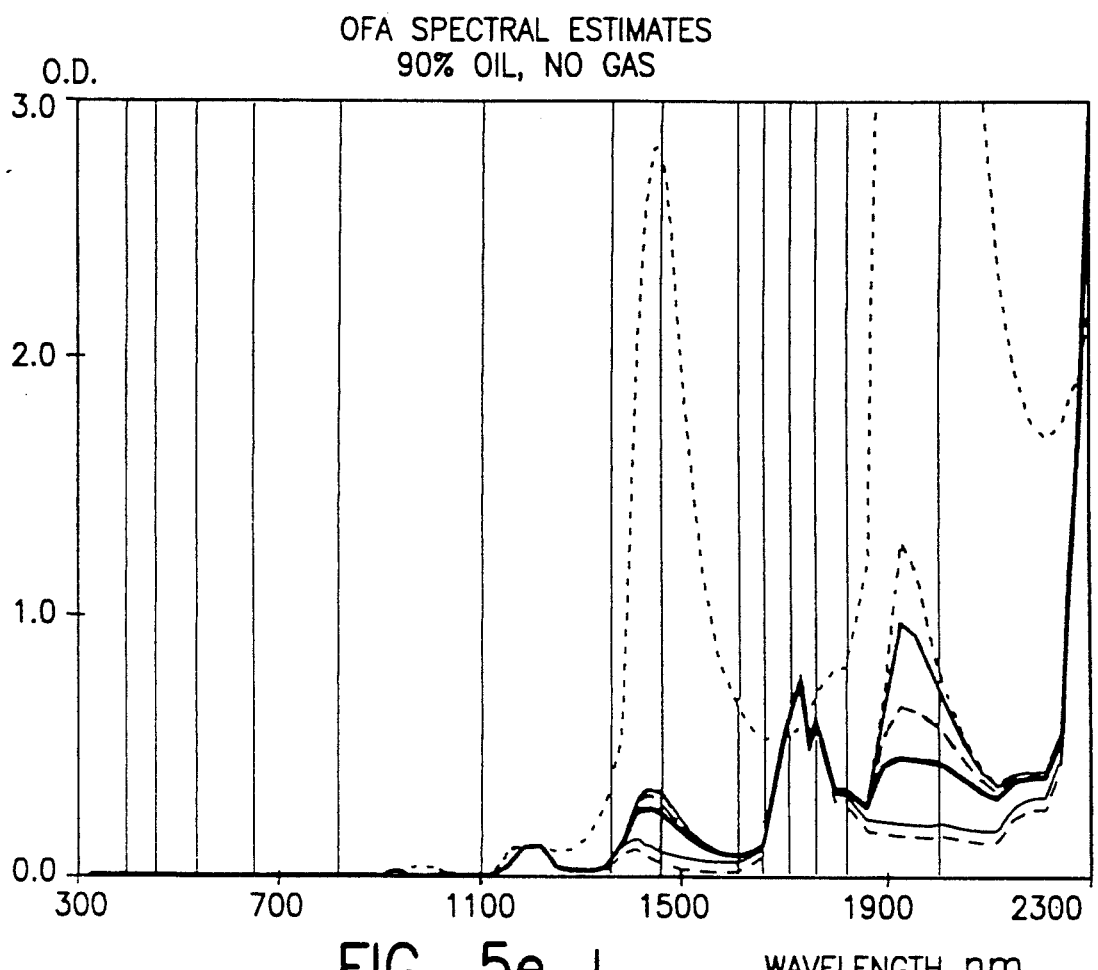
Figures 2, 5E:
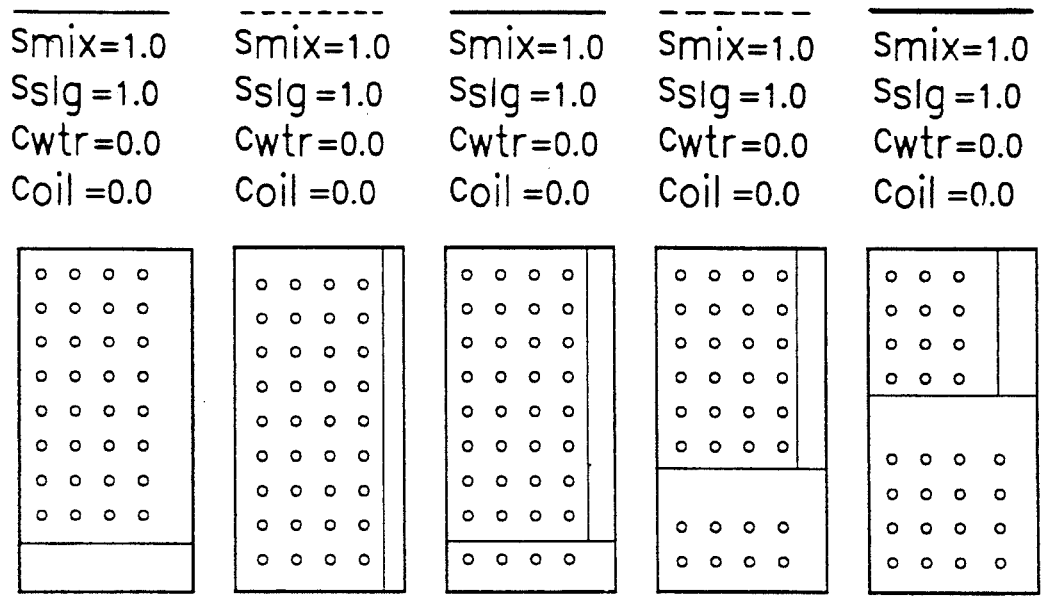

In the preferred embodiment of the invention, the wavelengths of choice in making the optical density measurements are 1710 and 1650 nanometers, as the absorption is linear with the oil and water fractions over that wavelength range. This may be seen with reference to FIGS. 5a-5e which are graphs showing the optical absorption curves of flow streams containing different percentages of slug and laminar flows, where the oil content is constant at 10%, 30%, 50%, 70% and 90% respectively. As seen in FIG. 5a, between the wavelengths of 1650 and 1710 nanometers, and regardless of the domain of the flow stream present (five different examples of which are shown in the key accompanying FIG. 5a), the optical absorption for a flow stream having 10% oil is substantially a function of wavelength and not the flow domain. This is seen by the convergence of the different lines (except for dashed pure oil and pure water curves which are for reference only) in that area. Turning to FIG. 5b, where the curves reference five different flow domains for flow streams containing 30% oil, it is seen that the curves converge in the 1650 to 1710 nanometer wavelengths. Comparing FIG. 5b to FIG. 5a, it is seen in the wavelengths of interest that the slope of the optical density curves for the flow streams containing 30% oil is greater than the slope of the optical density curves for the flow streams containing 10% oil. Turning to FIGS. 5c, 5d, and 5e, it is likewise seen that the curves of different sets of five different flow domains for the flow streams containing 50%, 70%, and 90% oil all converge in the 1650 to 1710 nanometer wavelength range, and that the slopes of the optical density curves increase as the percentage oil in the flow stream increases. Thus, it will be appreciated that in taking the difference of the optical density determinations at the 1650 and 1710 nanometer wavelengths, the larger the determined difference, the larger the percentage of oil in the flow stream. This corresponds to what is suggested by equation (9) above, and the relationship is seen to be linear for the wavelengths mentioned.

According to another aspect of the invention, the oil fraction of a flow stream is determined by first finding the amount of oil in the flow stream due to oil slugs, and that information is used in conjunction with the equations relating to laminar flow in order to find the amount of total amount of oil. In particular, oil slugs may be detected by finding the optical density of photons at a wavelength of approximately 1900 nm. Because water absorption at 1900 nm is extremely large, if any photons are detected, then water is not present at all, and an oil slug must be present. Over a length of flow stream, the transmission percentage (i.e., the percentage of the photons received) is therefore linearly related to the size (percentage) of the oil slugs.

Using the knowledge regarding oil slugs gained at the 1900 nm wavelength, two different methods may be used in order to determine the oil fraction in the flow stream. According to the preferred method, the oil spectrum relating to the oil slugs is removed (in log or linear form) from the transmission or optical density measurements made at 1710 and 1650 nanometers, and the techniques described above are used in order to determine what the oil and water fractions are in the remainder of the flow stream. The oil fraction in the remainder is then added to the percentage of oil slugs in the flow stream in order to find the oil fraction in the flow stream.

According to a second method, once the percentage of oil slugs in the flow stream is known, the remainder of the flow stream is considered to be in laminar flow, and equation (3) or (9) is used to describe the remainder of the flow stream. Using equation (3) or (9), any wavelength can be utilized to find the amount of oil in the laminar flow stream except for those wavelengths where oil and water have the same absorption and those wavelengths where either the oil absorption or water absorption is very large such that the presence of any water or oil would result in an optical density reading which was too large to properly detect. For example, while a wavelength of 1900 nm would not permit a proper determination of oil and water fractions because the water peak is too large, and a wavelength of 1710 would not permit a proper detection because the absorptions are too similar, the 1400 nm water peak (see FIG. 4) could be used. Based on the water and oil characteristics at 1400 nm, and using either equation (1) or (7), the amount of water and oil in the laminar flow portion of the flow stream is readily determined. Then, the oil slug fraction can be added to the oil fraction of the laminar flow portion to determine the oil and water fractions of the flow stream.

Figure 6A:
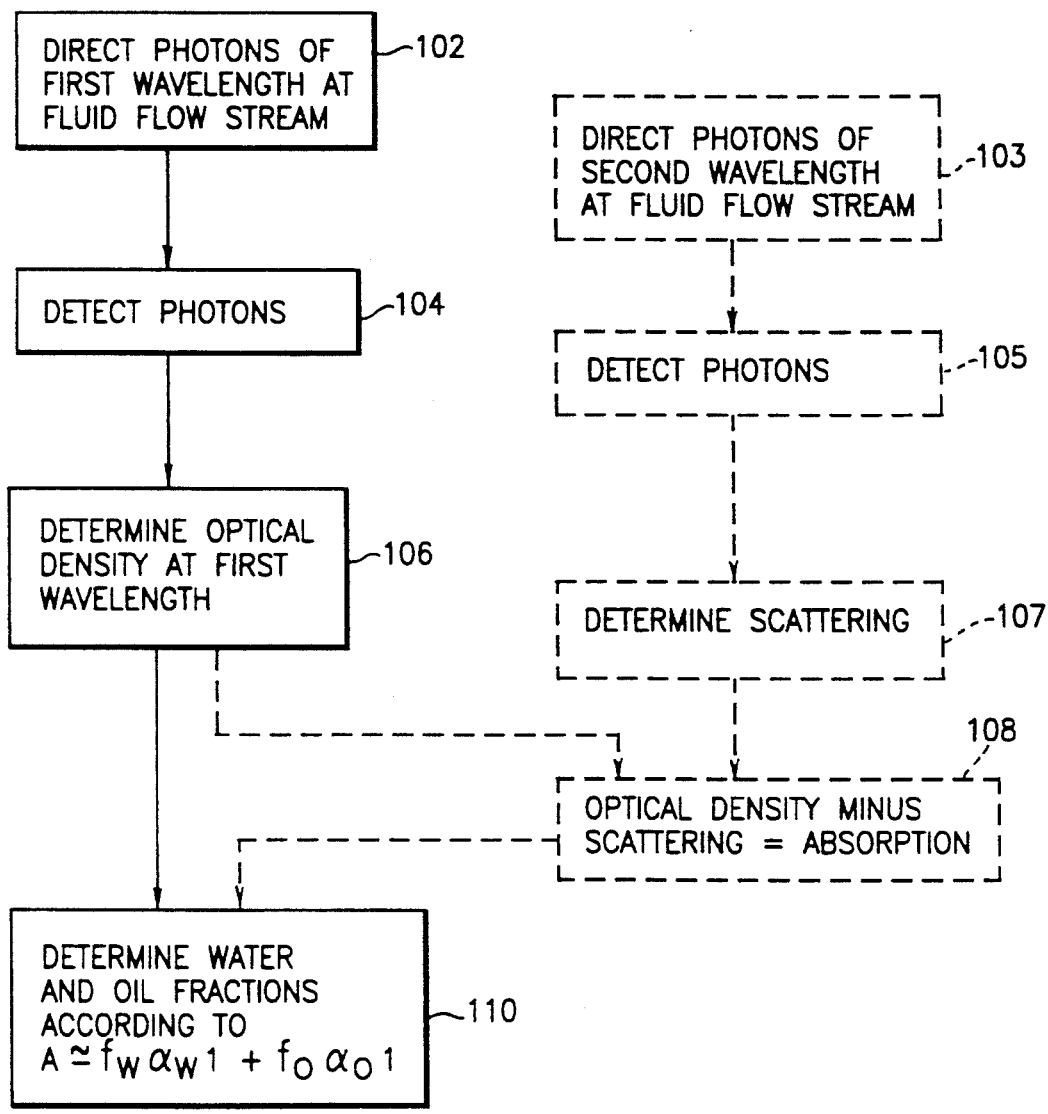
FIGS. 6a, 6b, and 6c are flow charts of first, second, and third methods of the invention for determining the oil and water fractions in a fluid flow stream.
Figure 6B:
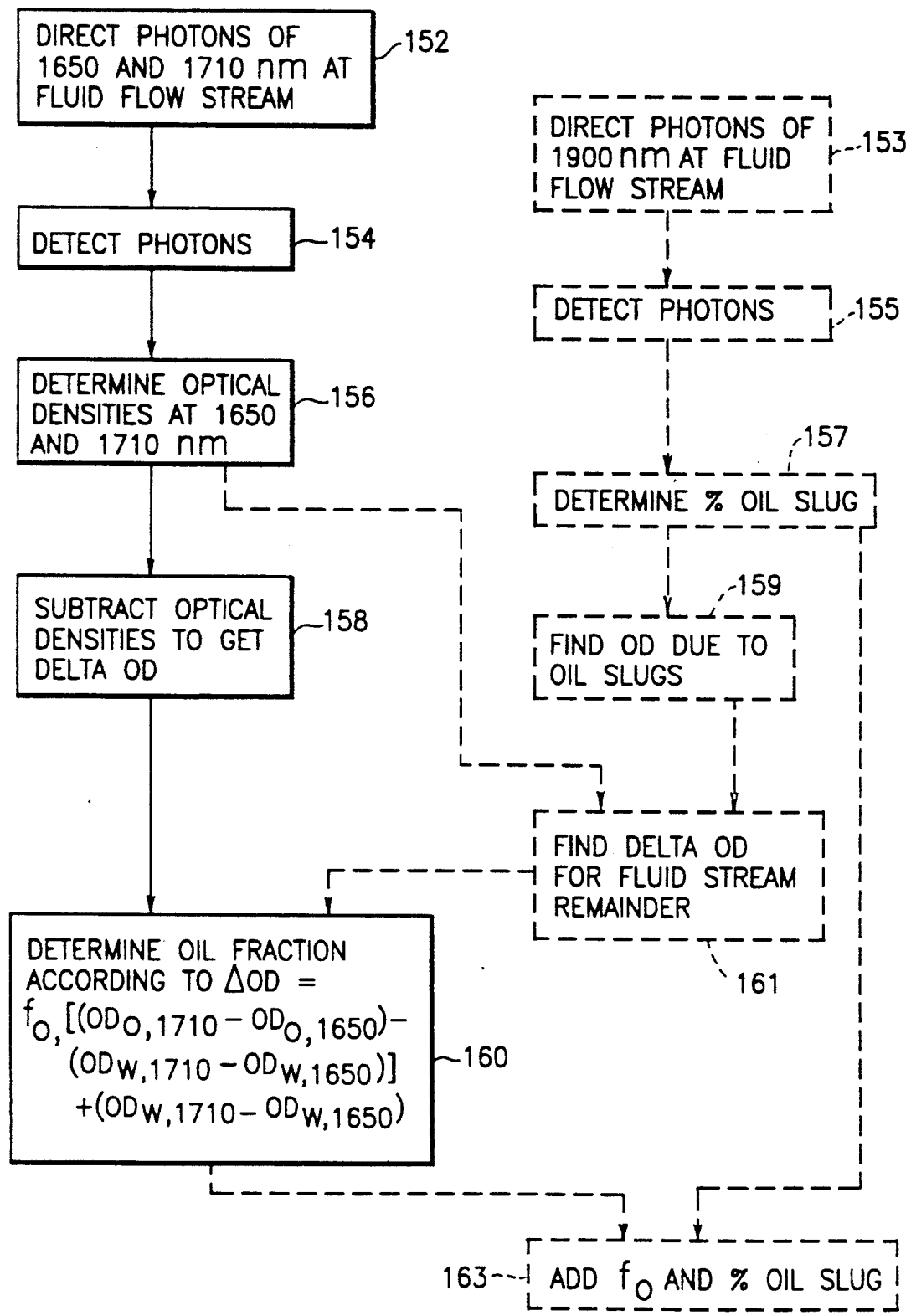
Figure 6C:
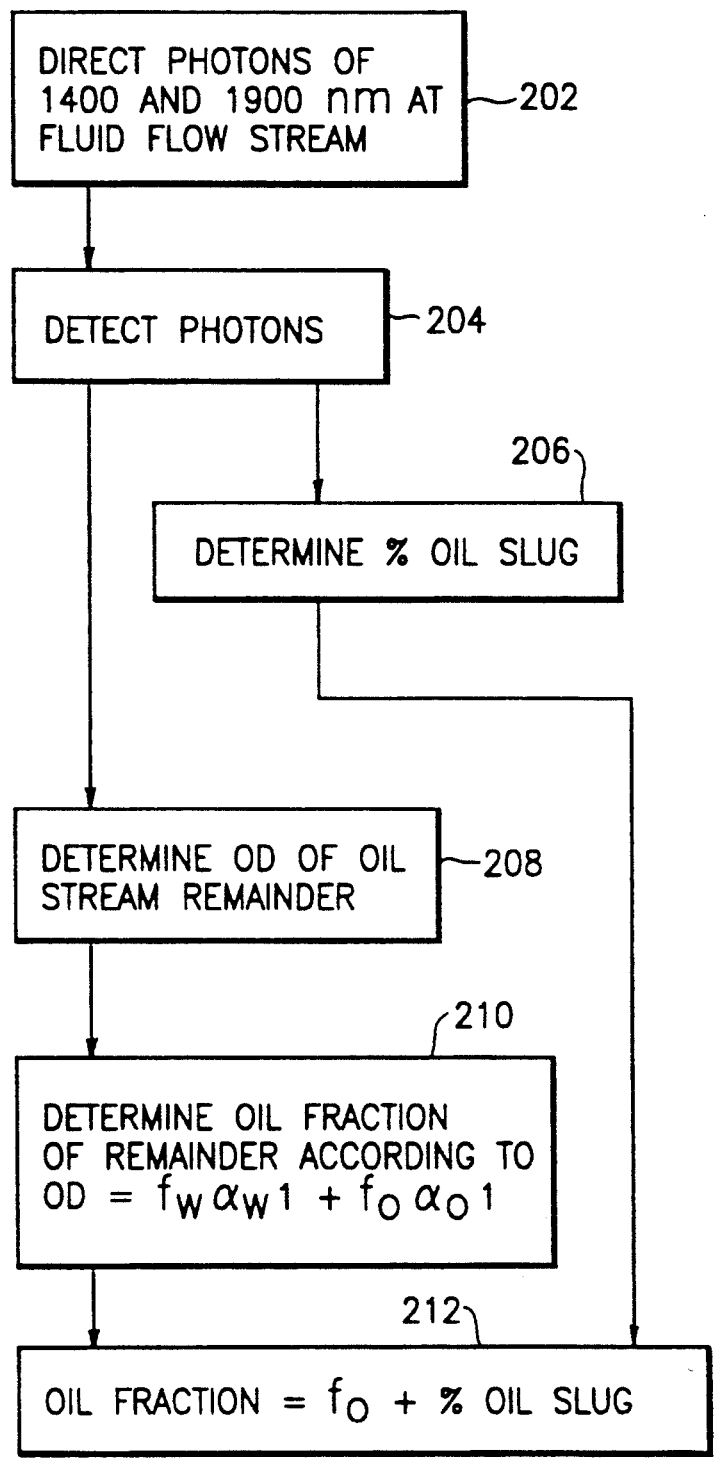

Turning to FIGS. 6a, 6b, and 6c, the methods set forth above for determining water and oil fractions of a flow stream are set forth in flow chart form. In FIG. 6a, at step 102, photons having a wavelength of about 1200, 1710, or 1735 nanometers are directed at a fluid flow stream. At step 104, the photons are detected by one or more detectors, and based on the number of photons directed at the fluid flow stream, and the number of photons detected, the optical density of the fluid flow stream is determined at step 106. Assuming that the determined optical density is due to absorption (as opposed to absorption plus scattering), and based on a knowledge of the thickness 1 of the fluid flow stream and the absorption characteristics of oil $\alpha_o$ and water $\alpha_w$ at the wavelength of the photons, the water and oil fractions are determined at 110 according to the equation $OD \simeq f_w \alpha_w 1 + f_o \alpha_o 1$ where $f_w$ is the water fraction, $f_o$ is the oil fraction, and $f_w + f_o = 1$.

As indicated in phantom in FIG. 6a, if desired, at step 103, photons of a wavelength where oil and water have very little absorption (e.g., 1100 nm) may be also directed at the flow stream, and detected at step 105. Based on the number of those photons directed and detected, the scattering S of the fluid flow stream is determined at step 107. Then, at 108, the scattering S determined at step 107 may be subtracted from the optical density determined at step 106 to provide the absorption. The absorption is then used at step 110 as indicated in order to determine the water and oil fractions.

Turning to FIG. 6b, at step 152, photons having wavelengths of about 1650 and 1710 nanometers are directed at a fluid flow stream. At step 154, the photons are detected by one or more detectors, and based on the number of photons directed at the fluid flow stream, and the number of photons detected, the optical density of the fluid flow stream for those wavelengths is determined at step 156. The optical density at 1650 nm is then subtracted from the optical density at 1710 nm at step 158 to yield a delta optical density. At step 160, the oil and water fractions are determined according to a linear equation which relates the delta optical density to the oil or water fraction. Preferably, at step 160, the oil fraction is determined according to $$\Delta OD = f_o[(OD_{o,a} - OD_{o,b}) - (OD_{w,a} - OD_{w,b})] + (OD_{w,a} - OD_{w,b})$$

where $f_o$ is the oil fraction, and $OD_{o,a}$, $OD_{o,b}$, $OD_{w,a}$, and $OD_{w,b}$ are respectively the optical densities of pure oil at wavelengths of 1710 nm and 1650 nm, and the optical densities of pure water at wavelengths of 1710 nm and 1650 nm. It will be appreciated by those skilled in the art that the 1710 nm and 1650 nm wavelengths utilized in FIG. 6b are by way of example, and other wavelengths could be utilized. It is required however, that the optical densities of oil and water at one of the wavelengths be similar, and that the other wavelength be chosen so that the delta optical density between the wavelengths be linear relative to the oil fraction in the flow stream.

As indicated in phantom in FIG. 6b, if desired, at step 153, photons of a wavelength where water has a very large absorption (e.g., 1900 nm) may be also directed at the flow stream, and detected at step 155. Based on the number of those photons directed and detected, the percentage oil slug of the fluid flow stream is determined at step 157. Then, at step 159, the optical density due to the oil slugs is determined for the wavelengths of interest (1710 and 1650 nm). This optical density is then subtracted at step 161 from the optical densities determined at step 156 to yield a delta optical density for the non-slug portion of the fluid stream. Thus, step 160 then yields the oil and water fractions for the non-slug portion of the fluid stream. At step 163, the oil fraction for the non-slug portion of the fluid stream is added to the percentage oil slug as determined at step 157 in order to provide an oil fraction and a fluid fraction for the fluid stream.

Turning to FIG. 6c, at step 202, photons having a wavelengths of about 1400 and 1900 nanometers are directed at a fluid flow stream. At step 204, the photons are detected by one or more detectors. At step 206, based on the number of photons detected at 1900 nm as opposed to the number directed at the fluid flow stream, a determination is made as to the percentage of oil slug of the fluid flow stream, with the percentage oil slug being directly related to the percentage of 1900 nm photons detected. As seen at step 208, a determination is also made as to the optical density (OD) at 1400 nm of the remainder of the fluid flow stream. Based on the determination made at step 208, the water and oil fractions of the remainder of the fluid flow stream are determined at 210. Preferably, the determination is made according to $I/I_0 = e^{-f_w \alpha'_w l} e^{-f_o \alpha'_o l}$ or $OD \simeq f_w \alpha_w l + f_o \alpha_o l$ where $f_w$ and $f_o$ are the water and oil fractions in the remainder of the fluid flow stream, l is the width of the fluid stream, and $\alpha'_o$ and $\alpha'_w$ are respectively the absorption characteristics of oil and water at 1400 nm ($\alpha_w = -\log_{10} \alpha'_w$, and $\alpha_o = \log_{10} \alpha'_o$). By adding at step 212 the determination made at step 210 as to the oil fraction of the remainder of the fluid flow stream with the determination made at step 206 as to the percentage oil slug, the oil fraction, and hence the water fraction of the fluid flow stream are determined.

There have been described and illustrated herein methods of analyzing oil and water fractions in a flow stream. While particular embodiments have been described, it is not intended that the invention be limited thereto, as it is intended that the invention be as broad in scope as the art will allow and that the specification be read likewise. Thus, while particular photon wavelengths were described as being preferred, it will be appreciated that other photon wavelengths could be utilized. For example, while one embodiment of the invention was described primarily with reference to a wavelength of 1710 nm, it will be appreciated that other wavelengths where the optical densities of oil and water are similar can be utilized. Similarly, while another embodiment of the invention was described primarily with reference to wavelengths of 1710 and 1650 nm, it will be appreciated that other wavelengths could be utilized provided that oil and water have similar optical densities at one of the wavelengths, and the other wavelength is sufficiently close to the first wavelength such that absorption is substantially linear with the oil (or water) fraction of the flow stream over the wavelength interval of interest. Also, while a third embodiment of the invention was described primarily with reference to wavelengths of 1900 and 1100 nm, it will be appreciated again that other wavelengths could be utilized provided that the optical density of water at one of the wavelengths is large so that any transmission of light will indicate the presence of an oil slug, and that the optical densities of water and oil at the other wavelength are different but readily measurable. Further, it will be appreciated that while particular apparatus for directing photons through a flow stream were described and referenced, particularly with reference to the borehole, it will be appreciated that other apparatus could be utilized both in and out of the borehole. It will therefore be appreciated by those skilled in the art that yet other modifications could be made to the provided invention without deviating from its spirit and scope as so claimed.

We claim:

1. A method of determining at least one of an oil fraction and a water fraction of a fluid flow stream having a width l, said method comprising:

a) directing a first number of photons of a first predetermined wavelength at said fluid flow stream, said first predetermined wavelength being chosen to be a wavelength where the absorptions of said oil and said water are substantially identical, wherein the absorption coefficients of said oil and said water at said wavelength are known;

b) detecting a second number of photons of said first predetermined wavelength which pass through said fluid flow stream; and c) determining, from said first number and second number, said width l, and said absorption coefficients of said oil and said water at said first predetermined wavelength, at least one of said oil fraction and said water fraction of said fluid flow stream.

2. A method according to claim 1, wherein:

said at least one of said oil fraction and said water fraction is determined at said determining step substantially according to $I/I_0 \simeq e^{-f_w \alpha'_w l} e^{-f_o \alpha'_o l}$ where I is said second number, $I_0$ is said first number, $f_w$ is said water fraction, $f_o$ is said oil fraction, $\alpha'_w$ is said absorption coefficient of said water at said first predetermined wavelength, $\alpha'_o$ is said absorption coefficient of said oil at said first predetermined wavelength, and $f_w + f_o = 1$.

3. A method according to claim 2, wherein:

said first predetermined wavelength is chosen from wavelengths of approximately 1200, 1710, and 1735 nanometers.

4. A method according to claim 3, wherein:

said first predetermined wavelength is approximately 1710 nanometers.

5. A method according to claim 1, wherein:

said first predetermined wavelength is chosen from wavelengths of approximately 1200, 1710, and 1735 nanometers.

6. A method according to claim 5, wherein:

said first predetermined wavelength is approximately 1710 nanometers.

7. A method according to claim 1, further comprising:

d) directing a third number of photons of a second predetermined wavelength at said fluid flow stream, said second predetermined wavelength being chosen to be sufficiently close to said first predetermined wavelength such that the absorption of said flow stream is substantially linear with the oil fraction of said flow stream to photons having wavelengths between said first and second wavelengths, wherein said absorption coefficients of said water and said oil are known at said second predetermined wavelength; and e) detecting a fourth number of photons of said second predetermined wavelength which pass through said fluid flow stream, wherein said determining step further utilizes said third and fourth numbers and said absorption coefficients of said water and said oil at said second predetermined wavelength.

8. A method according to claim 7, wherein:

said at least one of said water fraction and said oil fraction is determined at said determining step according to $$\Delta OD = f_o[(OD_{o,a} - OD_{o,b}) - (OD_{w,a} - OD_{w,b})] + (OD_{w,a} - OD_{w,b}),$$

where $OD_{o,a}$, $OD_{o,b}$, $OD_{w,a}$, and $OD_{w,b}$ are respectively said optical densities of said oil at said first wavelength and at said second wavelength, and said optical densities of said water at said first wavelength and at said second wavelength, $f_o$ is said oil fraction, and $\Delta OD$ is the difference between a first quotient and a second quotient, said first quotient being the negative of a logarithm of said second number divided by said first number, and said second quotient being the negative of a logarithm of said fourth number divided by said third number.

9. A method according to claim 8, wherein:
both said water fraction and said oil fraction are determined according to $f_o+f_w=1$, where $f_w$ is said water fraction.

10. A method according to claim 8, wherein:
said first predetermined wavelength is chosen from wavelengths of approximately 1200, 1710, and 1735 nanometers.

11. A method according to claim 10, wherein:
said first predetermined wavelength is chosen to be approximately 1710 nanometers, and said second predetermined wavelength is chosen to be approximately 1650 nanometers.

12. A method according to claim 7, wherein:
said first predetermined wavelength is chosen from wavelengths of approximately 1200, 1710, and 1735 nanometers.

13. A method according to claim 12, wherein:
said first predetermined wavelength is chosen to be approximately 1710 nanometers, and said second predetermined wavelength is chosen to be approximately 1650 nanometers.

14. A method according to claim 7, further comprising:
f) directing a fifth number of photons of a third predetermined wavelength at said fluid flow stream, said third predetermined wavelength being chosen to be a wavelength where the optical density of said water is very large; and
g) detecting a sixth number of photons of said third predetermined wavelength which pass through said fluid flow stream, wherein said sixth number divided by said fifth number provides an indication of the percentage of said fluid flow stream comprised of oil slugs, wherein said fluid flow stream is comprised of said oil slugs and a fluid flow stream remainder.

15. A method according to claim 14, wherein:
said at least one of said water fraction and said oil fraction is determined at said determining step according to $$\Delta OD = f_o[(OD_{o,a}-OD_{o,b})-(OD_{w,a}-OD_{w,b})] + (OD_{w,a}-OD_{w,b}),$$

where $OD_{o,a}$, $OD_{o,b}$, $OD_{w,a}$, and $OD_{w,b}$ are respectively said optical densities of said oil at said first wavelength and at said second wavelength, and said optical densities of said water at said first wavelength and at said second wavelength, $f_o$ is said oil fraction of said fluid flow stream remainder, and $\Delta OD$ is the difference between a first quotient and a sum of a second quotient and an optical density representing said oil slugs, said first quotient being the negative of a logarithm of said second number divided by said first number, said second quotient being the negative of a logarithm of said fourth number divided by said third number.

16. A method according to claim 14, wherein:
said first predetermined wavelength is chosen from wavelengths of approximately 1200, 1710, and 1735 nanometers, and
said third predetermined wavelength is approximately 1900 nanometers.

17. A method according to claim 14, wherein:
said oil fraction in said fluid flow stream is equal to said percentage of said fluid flow stream comprised of oil slugs plus $f_o$.

18. A method according to claim 1, further comprising:
d) directing a third number of photons of a second predetermined wavelength at said fluid flow stream, said second predetermined wavelength being chosen to be a wavelength where both said oil and said water have very little absorption; and
e) detecting a fourth number of photons of said second predetermined wavelength which pass through said fluid flow stream, wherein said determining step further utilizes said third and fourth numbers.

19. A method according to claim 18, wherein:
said at least one of said oil fraction and said water fraction is determined at said determining step according to $OD \approx f_w \alpha_w l + f_o \alpha_o l$ where OD is a difference between a first quotient and a second quotient, said first quotient being equal to the negative of a logarithm of said second number divided by said first number, and said second quotient being equal to the negative of a logarithm of said fourth number divided by said third number, and $f_w$ is said water fraction, $f_o$ is said oil fraction, $\alpha_w$ is related to said absorption coefficient of said water at said first predetermined wavelength, $\alpha_o$ is related to said absorption coefficient of said oil at said first predetermined wavelength, and $f_w+f_o=1$.

20. A method according to claim 18, wherein:
said first predetermined wavelength is chosen from wavelengths of approximately 1200, 1710, and 1735 nanometers.

21. A method according to claim 20, wherein:
said second wavelength is chosen to be approximately 1100 nanometers.

22. A method according to claim 1, further comprising:
d) directing a third number of photons of a second predetermined wavelength at said fluid flow stream, said second predetermined wavelength being chosen to be a wavelength where the optical density of said water is very large; and
e) detecting a fourth number of photons of said second predetermined wavelength which pass through said fluid flow stream, wherein said fourth number divided by said third number provides an indication of the percentage of oil slugs in said fluid flow stream.

23. A method according to claim 22, wherein:
said step of determining further utilizes said third and fourth numbers.

24. A method according to claim 23, wherein:
said second predetermined wavelength is approximately 1900 nanometers.

25. A method of determining at least one of an oil fraction and a water fraction of a fluid flow stream having a width l, said method comprising:
a) directing a first number of photons of a first predetermined wavelength at said fluid flow stream, said first predetermined wavelength being chosen to be a wavelength where the optical density of said water is very large;

b) detecting a second number of photons of said first predetermined wavelength which pass through said fluid flow stream;

c) directing a third number of photons of a second predetermined wavelength at said fluid flow stream, said second predetermined wavelength being chosen to be a wavelength where the optical densities of said water and said oil per unit path length are different from each other and neither is very large;

d) detecting a fourth number of photons of said second predetermined wavelength which pass through said fluid flow stream; and e) determining, from said first, second, third, and fourth numbers, said width l, and the absorption coefficients of said oil and said water at said second predetermined wavelength, at least one of said oil fraction and said water fraction of said fluid flow stream.

26. A method according to claim 25, wherein:
said second number divided by said first number provides an indication of the percentage of said fluid flow stream comprised of oil slugs, wherein said fluid flow stream is comprised of said oil slugs and a fluid flow stream remainder.

27. A method according to claim 26, wherein:
an oil fraction of said fluid flow stream remainder is determined according to one of $$I/I_0 = e^{-f_w \alpha_w l} e^{-f_o \alpha_o l}$$

and $$OD \approx f_w \alpha_w l + f_o \alpha_o l$$

where $f_w$ and $f_o$ are said water and oil fractions of said fluid flow stream remainder, and $\alpha_o'$ and $\alpha_w'$ are respectively the absorption coefficients of oil and water at said second predetermined wavelength, and $\alpha_o = \alpha_o' \cdot \log_{10} e$, and $\alpha_w = \alpha_w' \cdot \log_{10} e$.

28. A method according to claim 27, wherein:
said oil fraction in said fluid flow stream is equal to said oil fraction of said fluid flow stream remainder plus said oil slug percentage.

29. A method according to claim 25, wherein:
said first and second predetermined wavelengths are approximately 1900 nanometers and 1400 nanometers respectively.

* * * * *